(12) United States Patent
Isogai et al.

(10) Patent No.: US 6,668,662 B2
(45) Date of Patent: Dec. 30, 2003

(54) VISCOELASTICITY MEASURING DEVICE

(75) Inventors: Hiromichi Isogai, Shibata (JP); Katsuyoshi Kojima, Shibata (JP); Takayuki Masunaga, Yokohama (JP)

(73) Assignee: Toshiba Ceramics Co., Ltd., Tokyo (JP)

( * ) Notice: Subject to any disclaimer, the term of this patent is extended or adjusted under 35 U.S.C. 154(b) by 19 days.

(21) Appl. No.: 10/055,893

(22) Filed: Jan. 28, 2002

(65) Prior Publication Data

US 2002/0178795 A1 Dec. 5, 2002

(30) Foreign Application Priority Data

May 31, 2001 (JP) .................................. 2001-164407

(51) Int. Cl.⁷ ................................................ G01D 1/16
(52) U.S. Cl. ....................................................... 73/790
(58) Field of Search .......................... 73/760, 777, 788, 73/790, 813

(56) References Cited

U.S. PATENT DOCUMENTS

| | | | | |
|---|---|---|---|---|
| 5,269,190 A | * | 12/1993 | Kramer et al. ................. | 73/822 |
| 5,333,494 A | * | 8/1994 | Kishima et al. ............... | 73/788 |
| 5,569,858 A | * | 10/1996 | Askea et al. ................... | 73/789 |
| 5,610,325 A | * | 3/1997 | Rajagopal et al. ......... | 73/54.39 |
| 6,178,822 B1 | * | 1/2001 | Manning ....................... | 73/668 |

OTHER PUBLICATIONS

International Standard, TC61 ISO 6721–2, Plastics—Determination of Dynamic Mechanical Properties, International Standard for Standardization, First Edition, pp. 1–12, Nov. 1, 1994.

International Standard, TC61 ISO 6721–3, Plastics—Determination of Dynamic Mechanical Properties, International Standard for Standardization, First Edition, pp. 1–10, Nov. 1, 1994.

International Standard, TC61 ISO 6721–4, Plastics—Determination of Dynamic Mechanical Properties, International Standard for Standardization, First Edition, pp. 1–6, Nov. 1, 1994.

International Standard, TC61 ISO 6721–5, Plastics—Determination of Dynamic Mechanical Properties, International Standard for Standardization, First Edition, pp. 1–8, May 15, 1996.

International Standard, TC61 ISO 6721–6, Plastics—Determination of Dynamic Mechanical Properties, International Standard for Standardization, First Edition, pp. 1–7, May 15, 1996.

International Standard, TC61 ISO 6721–7, Plastics—Determination of Dynamic Mechanical Properties, International Standard for Standardization, First Edition, pp. 1–7, Jun. 1, 1996.

* cited by examiner

Primary Examiner—Max Noori
(74) Attorney, Agent, or Firm—Foley & Lardner

(57) ABSTRACT

The invention provides a viscoelasticity measuring device which is capable of imparting a desired displacement profile to a sample under conditions close to that of actual use. The viscoelasticity measuring device is composed of a presser to impart displacements to a sample; a rod to convey the displacements to the presser; a control jig kept in contact with an upper end portion of the rod and adapted to move to impart a desired displacement to the rod; a load cell which detects a load exerted to the sample to detect a stress generated in the sample; and a displacement sensor to detect the displacement in the sample; the displacements imparted of the sample being defined in accordance with a configuration and a moving speed of the control jig.

14 Claims, 4 Drawing Sheets

VISCOELASTICITY MEASURING DEVICE

BACKGROUND OF THE INVENTION

1. Field of the Invention

The present invention relates to a viscoelasticity measuring device to measure viscoelasticity properties and particularly to a viscoelasticity measuring device to measure viscoelasticity properties by imparting a displacement profile to a sample presser.

2. Description of the Related Art

Conventionally, there have been various methods proposed to measure viscoelasticity. As a means for conducting a measurement of static viscoelasticity, there are, for example, a stress relaxation measuring method in which a certain strain is imparted to a sample to measure a changing stress, a creep measuring method in which a certain stress is imparted to a sample to measure a changing strain, a stress/strain measuring method in which a certain strain speed is imparted to a sample, etc.

As a means for conducting a dynamic viscoelasticity measurement, there are Torsion-pendulum method (ISO6721 part 2, JIS K7244-2), Flexural vibration—Resonance-curve method (ISO6721-3), Tensile vibration—Non-resonance method (ISO6721-4), Flexural vibration—Non-resonance method (ISO6721-5), Shear vibration—Non-resonance method (ISO6721-6), Torsional vibration—Non-resonance method (ISO6721-7), and so on.

These measuring processes are being used in the field of semiconductor manufacturing; for example, in the measurement of the viscoelasticity properties of an abrasive cloth used for polishing semiconductor wafers or the like.

Such abrasive cloths used for polishing semiconductor wafers are in general made of polymeric materials of various properties and structures, including polyester non-woven cloths or foam polyurethane sheets.

The mechanical properties and particularly viscoelastic behaviors of such abrasive cloths can seriously affect the distribution of pressure exerted to materials to be polished (such as semiconductor wafers) to such an extent it is known that the materials, structures and viscoelastic properties after aging of the abrasive cloths influences the abrasive accuracy of the materials to be polished.

Therefore, abrasive cloths have so far been subjected to various viscoelasticity measurements.

Conventionally and in general, the viscoelasticity measurement of the abrasive cloths used for polishing the semiconductor wafers or the like was conducted on the basis of the measurement of hourly change in their deformation, that is, a creep deformation of the abrasive cloths was measured under a certain load thereof.

In the static measurement, however, it was impossible to realize conditions for imparting a forced displacement in an extremely short time and eliminating the conditions in an extremely short time in the static measurement and to conduct measurements under repeated loads other than stable vibrations in the creep measurement.

On the other hand, the behaviors of the abrasive cloths observed at the time of actual abrasion works are repeated in the form of forced displacement and recovery. Therefore, a means for measuring the viscoelasticity of the abrasive cloths under the condition similar to the actual behaviors of the abrasive cloth during the abrasion operation has long been wished for.

As one means for measuring the viscoelastic behaviors of abrasive cloths used for polishing semiconductor wafers or the like, the forced displacement measuring method may be considered. Therefore, the case of conducting measurements by the forced displacement measuring methods will be explained referring to FIG. 5, which shows the general structure of the conventional measuring device.

In the figure, the numeral 21 denotes a stage which is adapted to vertically move and support a sample 22 thereon. Above the sample 22, there is provided a rod 23 with an upper end portion thereof secured and a lower end face thereof attached with a load cell 24. Upon the upper surface of the sample 22, there is provided a presser 25 adapted to press the sample 22, the presser having an upper end portion adapted to contact the load cell 24.

Further, the stage 21 is attached with a stand 26, which has a tip portion provided with a laser displacement meter 27 to indicate the displacement of the sample 22 by measuring the displacement of the presser 25.

Then, the above arrangement is adapted to obtain viscoelastic properties by placing the sample 22 on the stage 21 and the presser 25 on the sample 22. At this time, care is to be taken to bring the upper portion of the presser 25 into contact with the load cell 24. Thus arranged, the laser displacement meter 27 is subjected to an origin correction such that the resultant position is defined as an origin thereof.

Thereafter, the stage 21 is vertically reciprocated to displace the same such that the measurement is started. The displacement of the sample is measured by the laser displacement meter 27. In addition, the load generated by the displacement and applied to the sample 22 by the presser is measured by the load cell 24.

Then, the stress generated in the sample is sought in addition to obtaining the displacement. More specifically, the measurement result of the viscoelasticity properties of the abrasive cloth used for polishing the semiconductor wafer is shown in FIG. 6.

As will be understood from the FIG. 6, the viscoelasticity properties of the abrasive cloth indicates that an increased displacement causes an increased stress to such an extent that the stress reducing to nil will not reduce the displacement to nil.

In this connection, there is a problem that the FIG. 5 device compresses the sample (the abrasive cloth) but will not cause no immediate displacement the moment a load is applied due to a problem of accuracy concerning the speed and position controls of the vertical stage reciprocation because of the vertical mechanism used in the stage.

Particularly, as the stress increase is limited at the time of the compression (or displacement), there remains a technical problem that the result is different from the viscoelastic properties under the actual use conditions.

In this way, the device fails to offer the displacement profile equal to that under a condition similar to the actual use conditions with the result that the technical problem means it is impossible to measure viscoelastic properties under a condition close to the actual use conditions.

SUMMARY OF THE INVENTION

The present invention is directed to solving the above described technical problems and to provide a viscoelasticity measuring device which imparts a desired displacement profile to a sample such that its viscoelastic behaviors under a use condition close to the actual use conditions.

The viscoelasticity measuring device according to the present invention which imparts a sample a predetermined displacement to measure a resultant displacement and stress comprises a presser to impart displacements to a sample; a rod to convey the displacements to the presser; a control jig kept in contact with an upper end portion top of the rod and adapted to move to impart a desired displacement to the rod; a load cell which detects a load exerted to the sample to detect a stress generated in the sample; and a displacement sensor to detect the displacement of the sample; the displacements imparted to the sample being defined in accordance with a configuration and a moving speed of the control jig.

In this way, as the displacement imparted to the sample is defined by the configuration of the control jig and its moving direction, the movement of the control jig will impart the displacement profile to the sample.

Therefore, the elimination of vertical movement as done in a stage in the conventional device will minimizes the adverse effect of inertia such that precise speed and position controls are ensured. As a result, it is possible to impart a desired displacement to the sample and measure viscoelastic behaviors under conditions close to actual use conditions.

Here, it is preferred that a predetermined displacement is imparted to the sample by defining a desired configuration to be imparted to the sample by means of the control jig while allowing the control jig to move at a predetermined moving speed in a plane perpendicular to an axis of the rod.

It is to be noted that a configuration of the control jig can produce different displacement profiles depending on the moving speed thereof. Therefore, it is preferred that not only the configuration of the control jig but also the moving speed is defined in order to impart the sample a predetermined displacement profile.

For example, it is possible to measure the viscoelastic properties under a condition imparting a forced displacement in an extremely short time or a condition removing a displacement imparted in an extremely short time by allowing the control jig at a high speed.

Further, it is preferred that the control jig is adapted for reciprocal movement, the reciprocal movement of the control jig repeatedly imparting forced displacements to the sampler and releasing the load therefrom.

In this way, it is possible to measure the viscoelastic properties under a condition imparting repeated loads to the sample because the control jig is adapted for reciprocal movement to impart repeated loads to the sample.

Then, it is preferred that the control jig is adapted to provide a configuration to define the displacements to be imparted to the sample, the control jig being adapted to move in a plane perpendicular to an axis of the rod at a predetermined speed such that the desired displacements are imparted to the sample.

It should be born in mind that even if the control jig has a similar configuration, the displacement profile imparted to the sample can differ depending upon the moving speed thereof. It is therefore preferred in order to impart a predetermined profile to the sample that not only the jig configuration but also the moving speed is defined. For example, a high speed movement of the jig ensures that the measurement of viscoelasticity is made possible under conditions imparting a forced displacement in an extremely short time or conditions eliminating the displacement imparted in an extremely short time.

Further, it is preferred that the control jig is adapted for reciprocal movement, the reciprocal movement of the control jig repeatedly imparting forced displacements to the sample and a release of load therefrom.

In this way, the control jig adapted for reciprocal movement and repeatedly imparted load to the sample ensure that the measurement of viscoelasticity under a condition imparting repeated displacements is conducted.

Further, it is also preferred that the control jig has a configuration to define the displacements to be imparted to the sample, the configuration having a portion which will not induce vertical actuation of the rod.

In this way, the provision of the portion which will not induce vertical actuation of the rod prevents the rod from stopping the movement during the course of the configuration of the jig such that the accurate repetition of the rod displacements is ensured. In other words, if the non-load condition and/or the maximum load condition reached at the portion which will not induce vertical actuation of the rod, an accurated condition can be brought about.

Here, it is preferred that the portion which will not give a (viz., induce or cause) vertical actuation of the rod is formed at opposite ends of the configuration of the control jig to define the displacements and in a plane parallel to the moving direction of the control jig.

DESCRIPTION OF THE PREFERRED EMBODIMENTS

Figure 1:
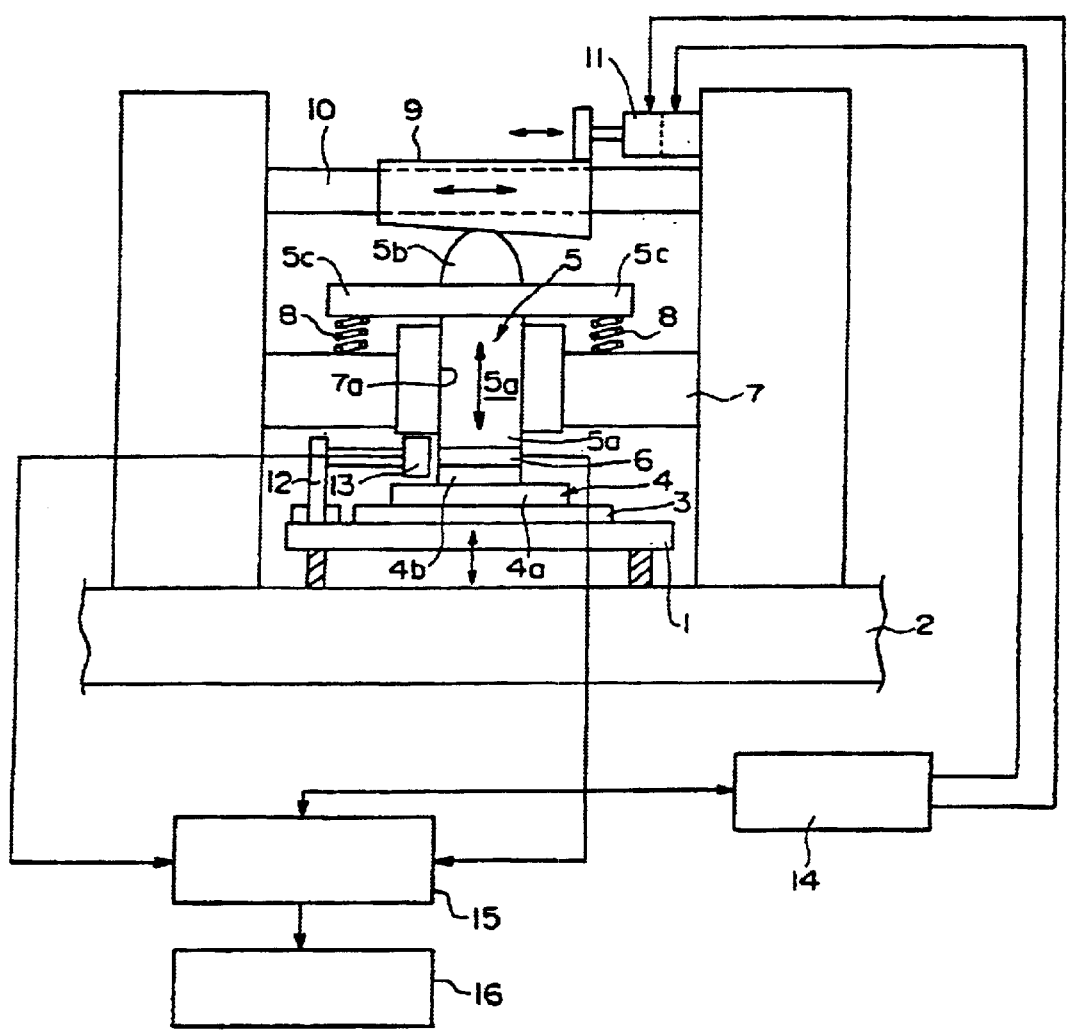
FIG. 1 is an outline illustration of the viscoelasticity measuring device in the form of one embodiment of the present invention.

The present invention will be explained with reference to FIG. 1 which shows one embodiment thereof in the form of a viscoelasticity measuring device. Here, FIG. 1 is an outline illustration of such device.

In the figure, the numeral 1 denotes a stage adapted to vertically reciprocate on the top surface of a base 2 while supporting a sample 3 thereon. Further, there is provided a presser 4 above the sample 3 to cause the same to displace, the presser 4 having a head 4a and a shaft 4b provided to stand upright on the head 4a.

Further, there is provided a rod 5 above the presser 4, the rod 5 having a shaft portion 5a provided with a load cell 6 at one end thereof, a semispherical slider 5b formed at the other end of the shaft portion 5a and a flange portion 5c extending in a direction perpendicular to the axis of the shaft portion 5a.

The shaft portion 5a of the rod 5 is held in a bore 7a of the support member 7 provided on the base 1 to reciprocate vertically. Then, there is further loaded a spring 8 between the lower face of the flange portion 5c and the upper face of the support member 7 to urge the rod 5 upwardly.

There is further provided a control jig 9 above the slider 5b of the rod 5 in contact with the slider 5b. The jig 9 is guided by a guide shaft 10 to reciprocate in a plane perpendicular to the axis of the rod 5. In other words, the guide shaft 10 is provided to extend perpendicularly to the axis of the rod 5. More specifically, the control jig 9 is adapted to move in directions from right to left and from left to right in the figure.

The movement or drive of the control jig 9 is caused by a piston of an air cylinder 11 attached to the control jig 9 to extend and retract.

The extension and retraction of the air cylinder 11 is prompted by the drive source 14 being controlled on the basis of control signals from the computer 15.

There is further formed a displacement in the periphery (or the face which the slider 5a of the rod 5 contacts) of the control jig 9 such that the lateral movement of the control jig 9 conveys a desired displacement profile in the head 4a of the presser 4.

Further, a stand 12 is attached to the stage 1, the stand 12 having a laser displacement meter 13 mounted at an end thereof to measure the displacement of the presser 4.

The displacement data from the laser displacement meter 13 and the load data from the load cell 6 are converted into a data formula to be inputted into a computer 15 by way of interface.

At the computer 15, the stress and displacement are calculated to be outputted to a printer 16, where the stress and displacement diagram is drawn. Although not shown, indication in the form of a CRT image is also acceptable.

In this connection, the deformation meter 13 may be of touch type.

Further, the drive of the control jig 9 is preferably done through a speed control by means of a pulse motor. In this case, a threaded shaft is provided in parallel with the guide shaft 10 such that the control jig 9 is screwed on the threaded shaft. Thus constructed, the threaded shaft is rotated by the pulse motor such that the control jig 9 is moved.

Further, the rod 5 is held by the spring 8 in constant contact with the control jig 9 but the spring 8 may be replaced with an air cylinder if the air cylinder assures the constant contact with the control jig.

Further, while the displacement profile of the control jig 9 of FIG. 1 is shown as having a tapered configuration, the shape is not limited thereto but a wave or an arced form is acceptable in order to obtain various profiles.

Figure 4:
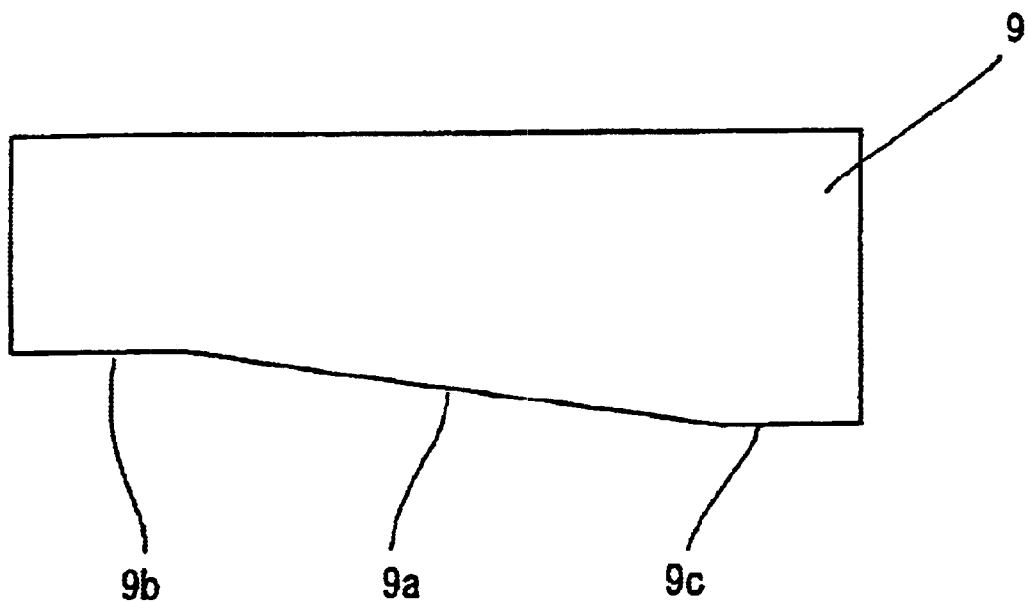
FIG. 4 is a side elevation of a modification of the control jig.
Figure 5:
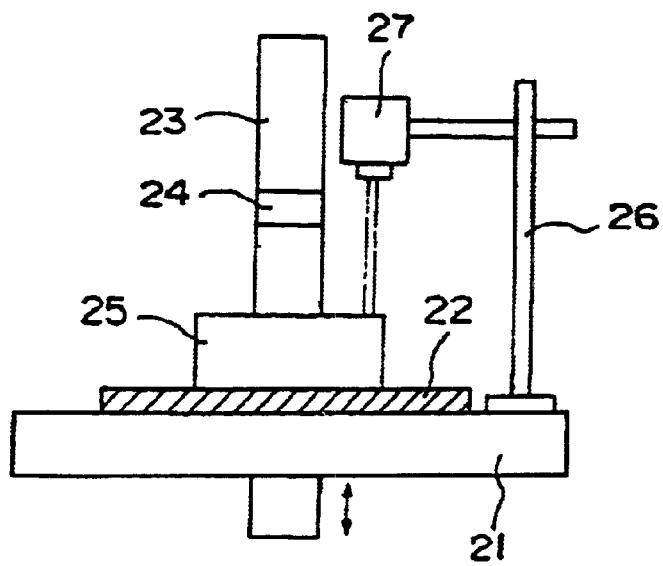
FIG. 5 is an outline illustration of the device used for the forced displacement measuring device.
Figure 6:
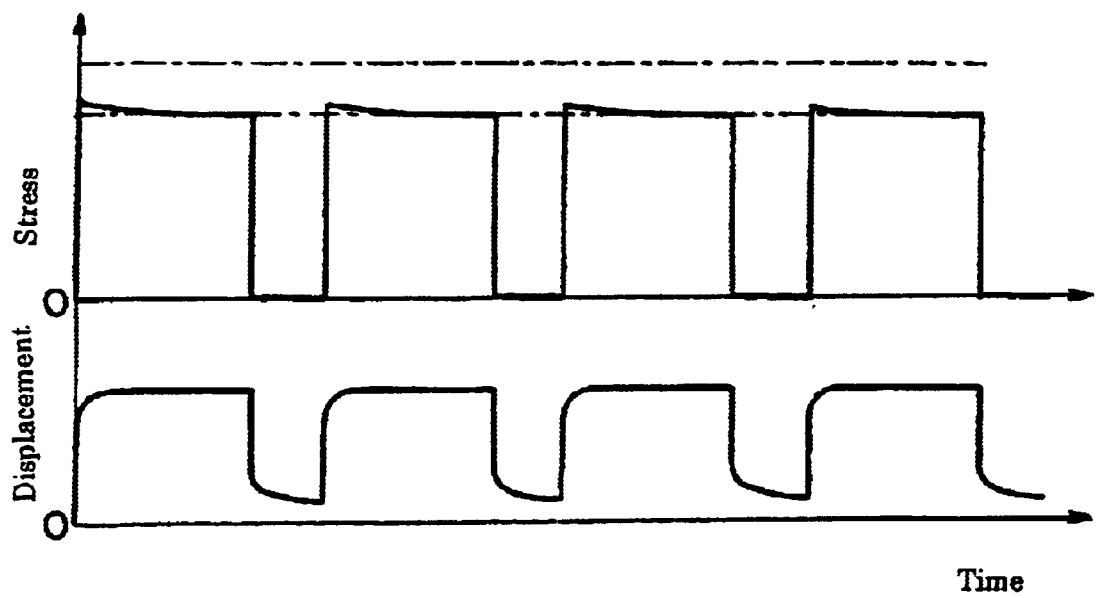
FIG. 6 shows a result of the measuring the viscoelasticity by means of the device shown in FIG. 5.

Further, the control jig 9 to define the displacement to be imparted to the sample is shaped such that portions 9a and 9b which will not vertically actuate the rod are preferably formed on both sides of a tapered portion 9a, that is, at opposite end portions of the control jig 9 as shown in FIG. 4. Further, the portions 9b and 9c which will not vertically actuate the rod extend in a plane parallel to a direction in which the jig 9 moves.

In this way, the provision of the portions 9b and 9c which will not vertically actuate the rod assures that the rod 5 will not stop intermediate the course of the control jig configuration, thus obtaining accurate repetition of the displacement of the rod 5. In other words, it ensures that a non-load state is brought about at the portion 9b while a maximum load state is brought about at the portion 9c.

As so far explained, the device is characterized in that the displacement of the presser 4 to press (or displace) the sample is imparted by the control jig 9 formed in advance with displacement profiles.

Next, the operation procedure of the device will be explained.

First, measurement conditions including displacements, displacement speeds, a load keeping time and a load release speed are determined to select the configuration of the control jig 9. Further, a slide speed to move the control jig 9 is inputted into the computer 15.

Further, the sample 3 is set on the stage 1, the presser 4 having a desired configuration in the surface thereof being set thereon in turn. The height of the stage 1 is adjusted to the level at which the underside of the sample 3 is in contact with the presser 4.

The contact of the presser 4 with the rod 5 will be detected by the load cell 6 attached to the rod shaft 5a such that the origin of the displacement sensor 13 attached to the stage 1 is corrected at a position of contact.

Then, the control jig 9 is moved to slide sideways under the condition preset to start the measurement.

In FIG. 1, as the control jig 9 is moved to left, the descending speed of the rod 5 is defined in accordance with its moving speed and the underside configuration of the jig 9, the displacement profile to compress the sample 3 is defined.

On the other hand, as the control jig 9 is moved to right, the ascending speed of the rod 5 is defined in accordance with its moving speed and the underside configuration of the jig 9, the ascending speed of the rod is defined to release the sample from the load.

It is to be noted in this connection that it is possible to measure the viscoelasitic behavior of the sample under the conditions of the forced displacement in a very short time, the forced displacement in a microscopic scale and the repeated forced displacement by changing the speed of lateral movements of the control jig 9 and an underside face thereof.

Then, the change in stress and displacement in the process thereof is measured by the load cells and the displacement sensor 13, respectively, such that the data thereof are outputted to the computer 15 where the stress and the displacement are computed.

The result of computation is outputted to the printer 16 such that the stress and displacement diagram is drawn by the printer 16 while the image thereof is represented at the CRT.

EXAMPLES

Example 1

By use of the device in accordance with the present invention, the viscoelasticity of the abrasive cloth used for semiconductor wafers is measured.

Figure 2:
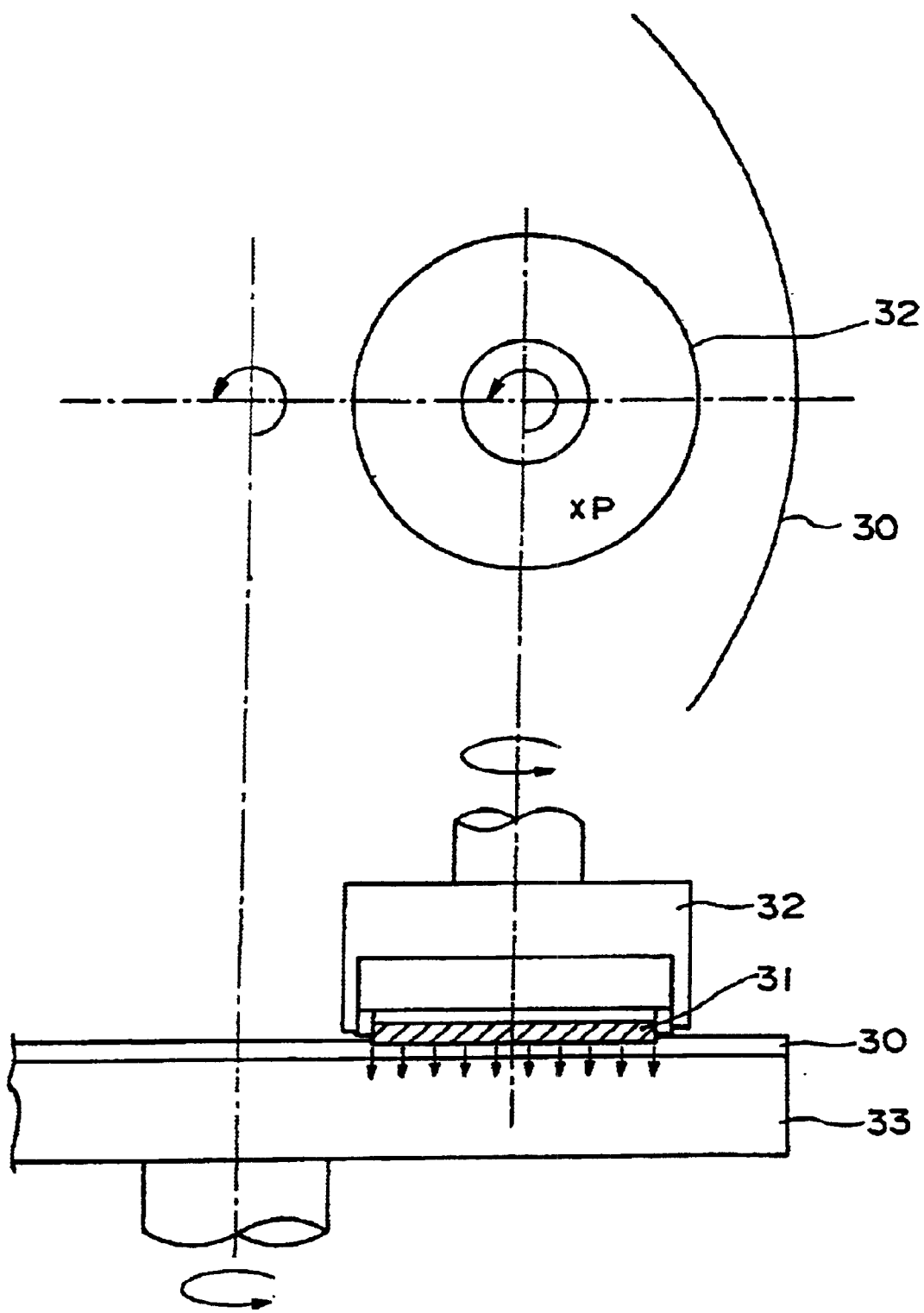
FIG. 2 is an illustration to explain an actual use condition of the abrasive cloth in a plan view and a side elevation of the abrasive device.

First, the abrasion work actually done will explained with reference to FIG. 2. The figure shows a point P in the abrasive cloth 30, which point the pressed wafer 31 passing the point repeatedly.

For example, with the revolution of the abrasion head 32 being 50 rpm, the revolution of the platen 33 being 50 rpm and the abrasion head 32 being without a swing action, the relative speed of the wafer 31 to that of the abrasive cloth being 1000 mm/sec. the time during which the abrasive cloth is being compressed each time the wafer 31 passes is 0.2 second or thereabout while the moment at which the cloth is compressed and the moment at which the cloth is released from the compression are as short as 0.5 millisecond.

Taking such condition of actual use into consideration, the viscoelastic behaviors of the abrasive cloth was measured by use of the device shown in FIG. 1.

Specifically, the moving speed of the control jig is set equal to the relative speed of the wafer to the abrasive cloth by using the control jig having a compression amount (displacement of the configuration) equal to the configuration of the end face of the wafer. Consequently, the forced displacement and recovery therefrom equal to the behavior of the abrasion cloth under the actual abrasion condition thereof are reproduced.

Figure 3:
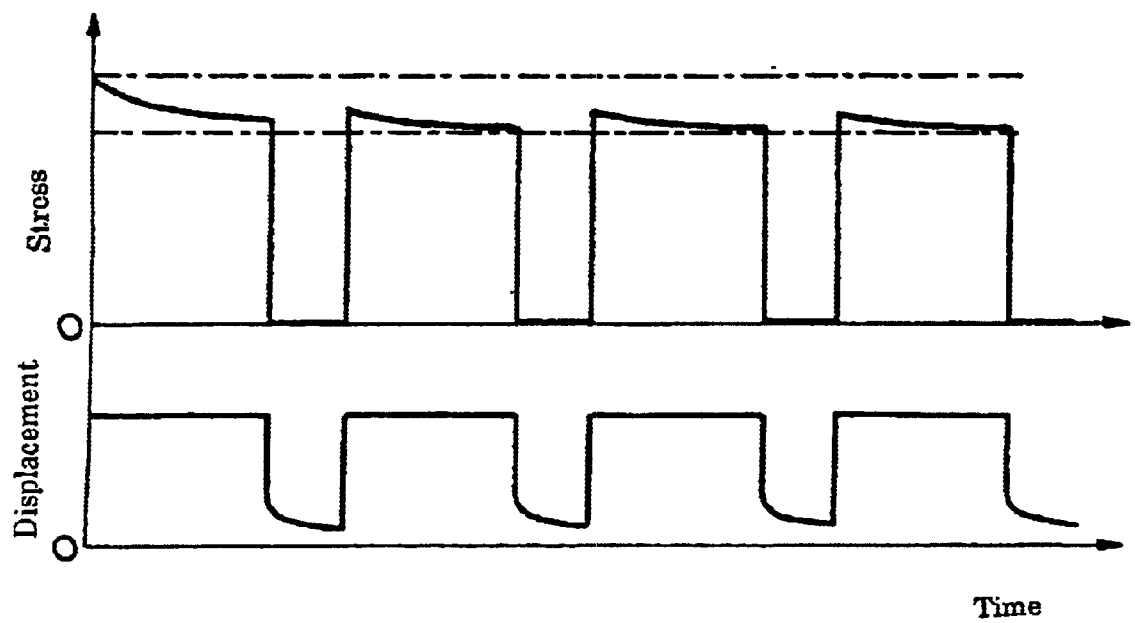
FIG. 3 shows the result of measurements conducted by means of the viscoelasticity measurement device in the form of the one embodiment of the present invention.

The relationship between the deformation and load obtained from this measurement is shown in FIG. 3.

As shown in FIG. 3, it is observed that the stress of the abrasive cloth is higher the moment the same is subjected to compression but decreases while being held. Further, as the compression is repeated twice, three times and more, the stress generated at the time of compression gradually decreases.

In other words, the moment the load is exerted thereon, it is observed that the displacement immediately takes place to indicate the stress increase shows itself at the time of compression (displacement) and that the viscoelasticity is similar to the actual use condition. In other words, the forced displacement profile is defined by the configuration of the control jig and its slide speed and it was confirmed that the predicted displacement profile was easily obtained.

According to the viscoelasticity measuring device according to the present invention, it is possible to give a desired displacement profile to the sample to assure measurements of the viscoelastic behavior under the conditions close to the actual use conditions.

What is claimed is:

1. A viscoelasticity measuring device which imparts a predetermined displacements to a sample to measure a resultant displacement and stress generated therewithin which comprises a presser to impart displacements to a sample;

a rod to convey said displacements to said presser, said rod having a semispherical upper portion;

a control jig kept in contact with an upper end portion of said rod and adapted to move in a plane perpendicular to an axis of said rod at a predetermined speed to impart a desired displacement to said rod;

a load cell which detects a load exerted to the sample to detect a stress generated in the sample;

a displacement sensor to detect the displacement of said sample; said control jig having a configuration and being adapted to be moved in a direction such that said displacement imparted to said sample is determined thereby.

2. A viscoelasticity measuring device as set forth in claim 1, wherein said control jig is adapted for reciprocal movement, said reciprocal movement of the control jig repeatedly imparting a forced displacement to the sample and a release of load therefrom.

3. A viscoelasticity measuring device as set forth in claim 2, wherein said configuration in the control jig has portions which will not induce vertical actuation of said rod, and wherein said portions are formed at opposite end portions of the configuration extending in a plane parallel to the moving direction of the control jig.

4. A viscoelasticity measuring device as set forth in claim 2, wherein said control jig is adapted for reciprocal movement, said reciprocal movement of the control jig repeatedly imparting forced displacements to the sample and a release of load therefrom.

5. A viscoelasticity measuring device as set forth in claim 1, wherein said control jig has a configuration to define the displacements to be imparted to the sample, said configuration having a portion which will not give a vertical actuation of said rod.

6. A viscoelasticity measuring device as set forth in claim 2, wherein said control jig has a configuration to define the displacements to be imparted to the sample, said configuration having a portion which will not give a vertical actuation of said rod.

7. A viscoelasticity measuring device as set forth in claim 3, wherein said portion which will not give a vertical actuation of said rod is formed at opposite end portions of the configuration of the control jig to define the displacements and in a plane parallel to the moving direction of the control jig.

8. A viscoelasticity measuring device as set forth in claim 4, wherein said control jig has a configuration to define the displacements to be imparted to the sample, said configuration having a portion which will not give a vertical actuation of said rod.

9. A viscoelasticity measuring device as set forth in claim 5, wherein said portion which will not give a vertical actuation of said rod is formed at opposite end portions of the configuration of the control jig to define the displacements and in a plane parallel to the moving direction of the control jig.

10. A viscoelasticity measuring device as set forth in claim 6, wherein said portion which will not give a vertical actuation of said rod is formed at opposite end portions of the configuration of the control jig to define the displacements and in a plane parallel to the moving direction of the control jig.

11. A viscoelasticity measuring device as set forth in claim 3, wherein said portion which will not give a vertical actuation of said rod is formed at opposite end portions of the configuration of the control jig to define the displacements and in a plane parallel to the moving direction of the control jig.

12. A viscoelasticity measuring device as set forth claim 8, wherein said portion which will not give a vertical actuation of said rod is formed at opposite end portions of the configuration of the control jig to define the displacements and in a plane parallel to the moving direction of the control jig.

13. A viscoelasticity measuring device as set forth in claim 5, wherein said portion which will not give a vertical actuation of said rod is formed at opposite end portions of the configuration of the control jig to define the displacements and in a plane parallel to the moving direction of the control jig.

14. A viscoelasticity measuring device as set forth in claim 6, wherein said portion which will not give a vertical actuation of said rod is formed at opposite end portions of the configuration of the control jig to define the displacements and in a plane parallel to the moving direction of the control jig.

* * * * *